(12) United States Patent
Schür

(10) Patent No.: US 7,638,114 B1
(45) Date of Patent: Dec. 29, 2009

US007638114B1

(54) METHOD FOR DISINFECTING THE AIR

(76) Inventor: Jörg Peter Schür, Heideweg 51, D-41844, Wegberg-Gladheim (DE)

( * ) Notice: Subject to any disclaimer, the term of this patent is extended or adjusted under 35 U.S.C. 154(b) by 1475 days.

(21) Appl. No.: 10/019,240

(22) PCT Filed: Jul. 7, 2000

(86) PCT No.: PCT/EP00/06462

§ 371 (c)(1), (2), (4) Date: May 13, 2002

(87) PCT Pub. No.: WO01/03746

PCT Pub. Date: Jan. 18, 2001

(30) Foreign Application Priority Data

Jul. 7, 1999 (DE) ................................ 199 31 185

(51) Int. Cl.
*A61K 9/12* (2006.01)
*A61K 36/00* (2006.01)
*A61L 9/00* (2006.01)
*A61L 2/00* (2006.01)

(52) U.S. Cl. .............................. 424/45; 422/4; 422/28; 422/725

(58) Field of Classification Search .................... 424/45
See application file for complete search history.

(56) References Cited

U.S. PATENT DOCUMENTS

| | | | |
|---|---|---|---|
| 1,331,331 A | 2/1920 | Erslev | |
| 1,790,596 A | 1/1931 | Schneible | |
| 2,409,088 A | 10/1946 | Weits | |
| 2,496,281 A | 2/1950 | Fisher | |
| 2,596,106 A | 5/1952 | Schneible | |
| 2,683,074 A | 7/1954 | Kuehner | |
| 2,886,297 A | 5/1959 | Crandall | |
| 3,191,363 A | 6/1965 | Martin, Jr. | |
| 3,363,403 A | 1/1968 | Vicard | |
| 3,442,602 A | 5/1969 | Diehl | |
| 3,518,096 A | 6/1970 | Layton | |
| 3,557,535 A | 1/1971 | Howick | |
| 3,788,045 A | 1/1974 | Arnold | |
| 3,908,031 A | 9/1975 | Wistreich | |
| 3,989,485 A | 11/1976 | Killian | |
| 4,110,430 A * | 8/1978 | Hopp et al. .................... | 424/65 |
| 4,200,442 A | 4/1980 | Willot | |
| 4,361,554 A | 11/1982 | Saunders | |
| 4,446,161 A | 5/1984 | Friedman | |
| 4,512,935 A | 4/1985 | Hilmersson | |
| 4,544,666 A | 10/1985 | Thirumalachar | |
| 4,579,569 A | 4/1986 | Sheng | |
| 4,602,011 A | 7/1986 | West | |
| 4,624,688 A | 11/1986 | Vatunen | |
| 4,806,526 A | 2/1989 | Green | |
| 4,808,396 A | 2/1989 | Shibanai | |
| 4,810,268 A | 3/1989 | Chambers | |
| 4,927,651 A | 5/1990 | Kumani | |
| 4,977,142 A | 12/1990 | Green | |
| 5,030,253 A | 7/1991 | Tokuhiro | |
| 5,089,268 A | 2/1992 | Katz | |
| 5,091,405 A | 2/1992 | Stevenson | |
| 5,143,720 A | 9/1992 | Lopes | |
| 5,201,919 A | 4/1993 | Jahn | |
| 5,322,689 A | 6/1994 | Hughes et al. | |
| 5,362,520 A | 11/1994 | Rodriguez | |
| 5,397,385 A | 3/1995 | Watts | |
| 5,416,075 A | 5/1995 | Carson et al. | |
| 5,439,690 A | 8/1995 | Knight | |
| 5,472,684 A | 12/1995 | Nabi | |
| 5,474,774 A | 12/1995 | Walker | |
| 5,480,519 A | 1/1996 | Abbott | |
| 5,480,591 A | 1/1996 | Lagneaux | |
| 5,527,552 A | 6/1996 | Todd, Jr. | |
| 5,547,540 A | 8/1996 | Ruscheweyh | |
| 5,569,461 A * | 10/1996 | Andrews ..................... | 424/405 |
| 5,591,395 A * | 1/1997 | Schroeder et al. .............. | 422/4 |
| 5,661,104 A | 8/1997 | Virgilio | |
| 5,665,432 A | 9/1997 | Kuwazuru | |
| 5,686,082 A | 11/1997 | N'Guyen | |
| 5,695,801 A | 12/1997 | Oh | |
| 5,747,416 A | 5/1998 | McArdle | |
| 5,750,563 A | 5/1998 | Honda | |
| 5,766,314 A | 6/1998 | Weber | |
| 5,814,325 A | 9/1998 | Rod | |
| 5,879,683 A | 3/1999 | Hamilton-Miller | |
| 6,004,569 A | 12/1999 | Bessette | |

(Continued)

FOREIGN PATENT DOCUMENTS

BE 515423 11/1952

(Continued)

OTHER PUBLICATIONS

DW 1976-72203, Sep. 1976, BE, Varga J.*

(Continued)

*Primary Examiner*—Christopher R Tate
*Assistant Examiner*—Randall Winston
(74) *Attorney, Agent, or Firm*—John S. Child, Jr.

(57) ABSTRACT

The invention relates to a method for disinfecting the air, comprising the distribution or atomization of a special antimicrobial composition. The invention also relates to antimicrobial compositions and the use thereof in order to disinfect the air.

21 Claims, 7 Drawing Sheets

U.S. PATENT DOCUMENTS

Figure 1:
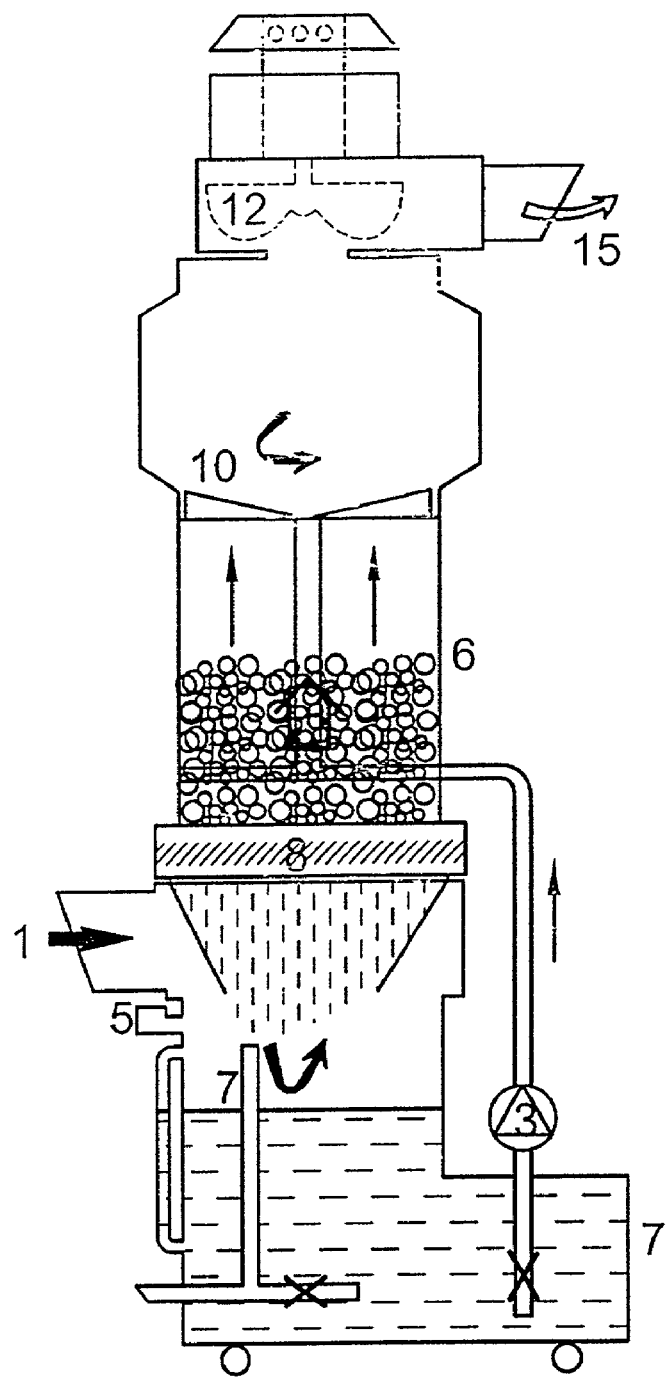

| | | | |
|---|---|---|---|
| 6,007,055 A | | 12/1999 | Schifftner |
| 6,033,705 A | * | 3/2000 | Isaacs ................. 426/323 |
| 6,086,904 A | * | 7/2000 | Crawford ............... 424/405 |
| 6,159,523 A | | 12/2000 | Cain |
| 6,207,290 B1 | | 3/2001 | Blum |
| 6,284,259 B1 | * | 9/2001 | Beerse et al. ........... 424/404 |
| 6,348,187 B1 | | 2/2002 | Pan |
| 6,514,551 B1 | | 2/2003 | Schür |
| 6,608,102 B1 | * | 8/2003 | Howell et al. .......... 514/456 |
| 2002/0014707 A1 | | 2/2002 | Zamany |
| 2002/0176882 A1 | | 11/2002 | Schür |
| 2003/0031588 A1 | | 2/2003 | Schür |
| 2003/0198718 A1 | | 10/2003 | Schür |
| 2004/0076614 A1 | | 4/2004 | Schur |
| 2004/0101459 A1 | | 5/2004 | Schür |
| 2005/0035472 A1 | | 2/2005 | Schur |

FOREIGN PATENT DOCUMENTS

| | | |
|---|---|---|
| CA | 2012288 | 9/1990 |
| CA | 2 336 565 | 1/2000 |
| CA | 2 355 595 | 5/2000 |
| CA | 2 376 517 | 1/2001 |
| CA | 2 378 043 | 1/2001 |
| CA | 2 382 429 | 3/2001 |
| CA | 2 382 740 | 3/2001 |
| CA | 2 450 745 | 12/2002 |
| DE | 2423076 | 5/1974 |
| DE | A-3409793 | 9/1984 |
| DE | A-3721137 | 1/1989 |
| DE | 3138277 A1 | 4/1992 |
| DE | 19612340 | 11/1996 |
| DE | 19617278 A1 | 11/1997 |
| DE | 19726429 A1 | 12/1998 |
| DE | 19831 288 A1 | 1/2000 |
| DE | 19831306 A | 1/2000 |
| DE | 19831309 A1 | 1/2000 |
| DE | 19931185 A1 | 1/2001 |
| DE | 19940283 A1 | 3/2001 |
| DE | 19940605 A1 | 3/2001 |
| DE | 20100121 U1 | 6/2002 |
| DE | 10100595 A1 | 7/2002 |
| DE | 10128563 | 1/2003 |
| DE | 10141734 A1 | 3/2003 |
| EP | 101083 | 2/1984 |
| EP | 0103878 A2 | 3/1984 |
| EP | A-0311091 | 4/1989 |
| EP | 0345149 A2 | 12/1989 |
| EP | 0557946 A1 | 9/1993 |
| EP | A-0687418 | 12/1995 |
| FR | 1400428 | 4/1965 |
| FR | 2228434 | 12/1974 |
| GB | 172993 | 4/1921 |
| GB | 790075 | 2/1958 |
| GB | 1060447 | 3/1967 |
| GB | 1 465 533 | 2/1977 |
| GB | 1571517 | 7/1980 |
| GB | 2 087 724 | 6/1982 |
| GB | 2 178 837 A | 2/1987 |
| JP | 60226992 | 11/1985 |
| JP | 6-211-1675 | 5/1987 |
| JP | 6-212-6931 | 6/1987 |
| JP | 2180267 A | 7/1990 |
| JP | 6-304-238 | 11/1994 |
| JP | 107304609 | 11/1995 |
| WO | WO 90/08543 A | 8/1990 |
| WO | WO-A-90/08544 | 8/1990 |
| WO | WO 94/14414 | 7/1994 |
| WO | WO 95/31100 | 11/1995 |
| WO | WO 96/29895 | 10/1996 |
| WO | WO-A-97/19683 | 6/1997 |
| WO | WO 98/21955 A1 | 5/1998 |
| WO | WO 98/54971 | 12/1998 |
| WO | WO 98/58540 | 12/1998 |
| WO | WO 00/03612 | 1/2000 |
| WO | WO 00/27192 | 5/2000 |
| WO | WO 01/03746 | 1/2001 |
| WO | WO 01/03747 | 1/2001 |
| WO | WO 01/13727 A1 | 3/2001 |
| WO | WO 01/15528 A1 | 3/2001 |
| WO | WO 02/053978 A1 | 7/2002 |
| WO | WO 02/055114 A1 | 7/2002 |
| WO | WO 02/101299 | 12/2002 |
| WO | WO 02/101299 A1 | 12/2002 |

OTHER PUBLICATIONS

Scalbert et al. (Antimicrobial properties of Tannins), Phytochemistry vol. 30, No. 12, pp. 3875-3883, 1991.*
Scalbert et al. (Antimicrobial properties of Tannins), Phytochemistry vol. 30, No. 12, pp. 3875-3883, 1991.).*
U.S. Appl. No. 09/743,883, filed Mar. 26, 2001, Jörg Peter Schür.
U.S. Appl. No. 10/019,239, filed May 13, 2002, Jörg Peter Schür.
U.S. Appl. No. 10/069,476, filed Jul. 1, 2002, Jörg Peter Schür.
U.S. Appl. No. 10/250,659, filed Jul. 3, 2003, Jörg Peter Schür.
U.S. Appl. No. 10/070,042, filed Jul. 18, 2002, Schur.
Database WPI, Section CH. Week 199411, Derwent Publications Ltd, London, GB; DW 94-088588 & JP 06038678 (Okubo T), Feb. 15, 1994.
Database WPI, Section CH, Week 199028, Derwent Publications Ltd, London, GB; AN 90-213153 & JP 02142703 (Kurita Water Ind KK) May 31, 1990.
Database WPI, Section CH, Week 198302, Derwent Publications Ltd, London, GB; AN 83-03563K & JP 57 194775, (Asama Kasei KK) Nov. 30, 1982.
Database WPI, Section CH, Week 198726 Derwent Publications Ltd, London, GB; AN 87-181806 & JP 62111675 (Sanraku Ocean) May 22, 1987.
Database WPI, Section CH, Week 198946 Derwent Publications Ltd, London, GB; AN 1989-337764, & SE 8 900902 (Thorsell W) May 13, 1989.
Database WPI, Section CH, Week 198728 Derwent Publications Ltd., London, GB; AN 1987-196269 & JP 62126931A (Morinaga Milk Co. Ltd) Jun. 9, 1997.
Database WPI, Section CH, Week 199049 Derwent Publications Ltd., London, GB; AN 1990-361964 & CA 2,012288A (Sterling Drug Inc.) Sep. 16, 1990.
Database WPI, Section CH, Week 197819 Derwent Publications Ltd., London, GB; AN 78-33903 A & JP 53032134A (Katsiraua Fine Goods) Mar. 27, 1978.
Database WPI, Section CH, Week 198621 Derwent Publications Ltd., London, GB; AN 86-136554 & SU 1189454A (Ural Vnipi Khim Promy) Nov. 7, 1985.
Japanese Patent Publication No. JP 46028797B, (1971), (cover sheet).
Database WPI, Section CH, Week 199216 Derwent Publications Ltd., London, GB; AW 1992-127230 & JP 04 069308A (Do1 K) Mar. 4, 1992.
Patent Abstracts of Japan vol. 014, No. 453 (C-0764) Sep. 28, 1990 JP 02 180267A (Matsushita Electric Works, Ltd) Jul. 13, 1990.
Chemical Abstracts: vol. 102; 165 387 u (1985), Arora, Rewa, Pandex, GN (HB Technical Inst., Kampur 208 002 India) Biol. Mem. 1984 9(1), 98-104 (Eng.).
Chemical Abstracts: vol. 107; 133021g (1987) Food Preservation Composition, Kummamoto, Toshihiko, JP 61 111675 [87 111 675] May 22, 1987.
Chemical Abstracts: vol. 117; 68848 x (1992), Kutsuwa, Yoshiaki (Asahi Denka Kogyo KK) UP 04 79869 [9279869] Mar. 13, 1992.
Chemical Abstracts: vol. 121; 33789; (1994) Sakai, Isao, JP 0678730 [94 78 730]. Mar. 22, 1999.
Kabara, Jon J. [Hrsg] Cosmetic and Drug Preservation, 1984, S 237-270; 275-297.
The Merck Index, Merck & Co., Inc. (Rahway, NJ, 1976), pp. 1172-1173.

Code of Federal Regulations, 21 C.F.R. § 182/515) and § 182.20 (Revised as of Apr. 1, 2001).

Mendez, B., et al., "Effects of Different Lipid Sources in Total Parenteral Nutrition on Whole Body Protein Kinetics and Tumor Growth", Journal of Parenteral and Enteral Nutrition, American Society for Parenteral and Enteral Nutrition, vol. 16: pp. 545-551 (1992).

Database WPI, Week 198517, Derwent Publications Ltd., London, Great Britain, AN 1985-103098 and JP 60 049747 A (San-Yu Shoji KK), Mar. 19, 1985. Abstract.

* cited by examiner

METHOD FOR DISINFECTING THE AIR

This application is a continuation-in-part of co-pending International Application No. PCT/EP00/06462 filed Jul. 7, 2000, which claims the benefit of that application under 35 U.S.C. § 120, and which claims the benefit under 35 U.S.C. § 119 of German Application No. 19931185.4, filed Jul. 7, 1999, and International Application No. PCT/EP00/02992, filed Apr. 4, 2000.

The present invention relates to a method for the disinfection of air, comprising the distributing or atomizing of a specific antimicrobial composition, to antimicrobial compositions suitable for this purpose, and the use of these compositions for the disinfection of air.

The germ load of the ambient air is a basic problem in private households and commercial office complexes as well as in plants of the producing trade, especially in food-processing plants, and packaging is also subject to exogenous and endogenous germ loads. Currently, this germ load is controlled, if it is at all, solely by a rapid exchange of air and sometimes by the use of air filtering systems. However, the effect achieved thereby is insufficient, and in particular, the filtering systems employed can themselves act as sources for the distribution of microorganisms within the ambient air. Solutions to this problem are currently being sought world-wide. However, the skilled persons involved agree upon the fact that a simple treatment with an antimicrobial substrate will not solve this problem since such a substance would become deposited on or incorporated into the food, on the one hand, or would result in a load on the respiratory organs.

Then again, the antimicrobial activity of compositions containing several GRAS (generally recognized as safe) flavoring agents is known from the documents WO 96/29895, WO 98/58590, DE-A-198 31 306, and WO 00/03612 (the latter two having been published after the priority date of the present application). Further, from the U.S. Pat. No. 4,806,526, it is known that aqueous ethanolic solutions (from 20 to 40% by volume of ethanol) containing from 0.1 to 10% by weight of tannic acid and optionally benzyl alcohol (from 5 to 20% by volume) have miticidal and anti-allergic properties and may also be applied in the form of aerosols.

However, especially when the method according to the invention is employed in food-processing plants or in inhabited rooms, it is necessary that the antimicrobial composition be free from ethanol and isopropanol or free from harmful doses of ethanol and isopropanol, since these substances can be inhaled by the people in the treated rooms. In addition, when such compounds are used, there may be danger of explosion.

Surprisingly, it has now been found that the germ content in the ambient air can be significantly reduced by distributing/atomizing a special antimicrobial composition which contains two or more GRAS flavoring agents and is free from ethanol and isopropanol. In addition, extremely low concentrations of the antimicrobial composition are required for the method to be effective, so that the composition will not cause any negative impact on the persons present in the room or on the products stored therein.

Accordingly, the present application relates to (1) a method for the disinfection of air, comprising the distributing or atomizing of an antimicrobial composition, wherein said antimicrobial composition is free from ethanol and isopropanol and contains (a) one or more GRAS (generally recognized as safe) flavor alcohols or their derivatives; and (b) one or more flavoring agents selected from
- (b1) polyphenol compounds; and
- (b2) GRAS flavor acids or their derivatives;

(2) a preferred embodiment of the method defined in (1), wherein said antimicrobial composition contains an aromatic GRAS flavor alcohol, especially benzyl alcohol, as a necessary component;

(3) an antimicrobial composition, especially a composition used for the disinfection of air as defined in (1) or (2); and (4) the use of the composition as defined in (3) for the disinfection of air.

FIGURES

The following Figures show devices which can be employed in the disinfection methods according to the invention.

FIG. 1 shows an air DOA (disinfection of air) bubbler.

FIGS. 2A, 2B and 2C show a two-fluid nozzle system.

FIG. 3 shows an evaporation system.

FIG. 4 shows a bubbler DOA device for disinfection within a package.

FIG. 5 shows the results of the experiment described in Example 4 with respect to the air germ content in a cheese maturing store as determined with and without the use of the method according to the invention.

FIG. 6 shows a schematic lateral view of the device for enriching air.

FIG. 7 shows a device which corresponds to the device represented in FIG. 6 with a pressure generating means provided downstream.

In the following, the components of the compositions according to the invention are described in more detail:

The mentioned GRAS flavor alcohols of component (a) are recognized by the FDA authority as commercially safe for use in foods (GRAS=generally recognized as safe in food). The mentioned GRAS flavor alcohols and also the other GRAS flavoring agents defined below are the compounds mentioned in the FEMA/FDA GRAS Flavour Substances Lists GRAS 3-15 Nos. 2001-3815 (as of 1997). This list contains natural and naturally occurring synthetic flavoring agents approved by the American public health authority, FDA, for use in foodstuffs: FDA Regulation 21 CFR 172.515 for naturally occurring synthetic flavoring agents (Synthetic Flavoring Substances and Adjuvants) and FDA Regulation 21 CFR 182.20 for natural flavoring agents (Natural Flavoring Substances and Adjuvants).

The antimicrobial composition defined above under (1) can contain from 0.1 to 99.9% by weight, preferably from 0.5 to 99% by weight, of component (a);

from 0 to 25% by weight, preferably from 0.01 to 10% by weight, of component (b1); and/or from 0 to 70% by weight, preferably from 0.01 to 30% by weight, of component (b2).

According to the invention, component (a) may contain one or more GRAS flavor alcohols. It is preferred according to the invention to use two or three GRAS flavor alcohols. In detail, the following GRAS flavor alcohols may be employed, for example:

benzyl alcohol, acetoin (acetylmethylcarbinol), propyl alcohol (1-propanol), propylene glycol, glycerol, n-butyl alcohol (n-propyl carbinol), iso-butyl alcohol (2-methyl-1-propanol), hexyl alcohol (hexanol), L-menthol, octyl alcohol (n-octanol), cinnamyl alcohol (3-phenyl-2-propene-1-ol), á-methylbenzyl alcohol (1-phenylethanol), heptyl alcohol (heptanol), n-amyl alcohol (1-pentanol), iso-amyl alcohol (3-methyl-1-butanol), anisalcohol (4-methoxybenzyl alcohol, p-anisalcohol), citronellol, n-decyl alcohol (n-decanol), geraniol, â-ã-hexenol (3-hexenol), lauryl alcohol (dodecanol), linalool, nerolidol, nonadienol (2,6-nonadiene-1-ol), nonyl alcohol (nonanol-1), rhodinol, terpineol, borneol, clineol (eucalyptol), anisole, cuminyl alcohol (cuminol), 10-undecene-1-ol, 1-hexadecanol. As said derivatives, both natural and synthetic (naturally occurring or not) derivatives can be employed. Suitable derivatives include, for example, the esters, ethers and carbonates of the above mentioned GRAS flavor alcohols. Particularly preferred GRAS flavor alcohols are benzyl alcohol, 1-propanol, glycerol, propylene glycol, n-butyl alcohol, citronellol, hexanol, linalool, acetoin and their derivatives.

As component (b1), the following polyphenols may be employed:

catechol, resorcinol, hydroquinone, phloroglucinol, pyrogallol, cyclohexane, usnic acid, acylpolyphenols, lignins, anthocyans, flavones, catechols, gallic acid derivatives (e.g., tannins, gallotannin, tannic acids, gallotannic acids), including derivatives of the above-mentioned compounds, such as (2,5-dihydroxy-phenyl)carboxylic and (2,5-dihydroxyphenyl)alkylenecarboxylic substitutions, salts, esters, amides; caffeic acid and its esters and amides, flavonoids (e.g., flavone, flavonol, isoflavone, gossypetin, myricetin, robinetin, apigenin, morin, taxifolin, eriodictyol, naringin, rutin, hesperidin, troxerutin, chrysin, tangeritin, luteolin, catechols, quercetin, fisetin, kaempferol, galangin, rotenoids, aurones, flavonols, flavonediols), extracts, e.g., from Camellia, Primula. Further, their possible derivatives, e.g., salts, acids, esters, oxides and ethers, may also be used. A particularly preferred polyphenol is tannin (a GRAS compound).

As component (b2), the following GRAS acids may be used, for example:

acetic acid, aconitic acid, adipic acid, formic acid, malic acid (1-hydroxysuccinic acid), capronic acid, hydrocinnamic acid (3-phenyl-1-propionic acid), pelargonic acid (nonanoic acid), lactic acid (2-hydroxypropionic acid), phenoxyacetic acid (glycolic acid phenyl ether), phenylacetic acid (á-toluenic acid), valeric acid (pentanoic acid), iso-valeric acid (3-methylbutyric acid), cinnamic acid (3-phenylpropenoic acid), citric acid, mandelic acid (hydroxyphenylacetic acid), tartaric acid (2,3-dihydroxybutanedioic acid; 2,3-dihydroxysuccinic acid), fumaric acid, tannic acid and their derivatives.

Suitable derivatives of the mentioned acids according to the present invention are esters (e.g., $C_{1-6}$-alkyl esters and benzyl esters), amides (including N-substituted amides) and salts (alkali, alkaline earth and ammonium salts). According to the present invention, the term "derivatives" also encompasses modifications of the side-chain hydroxy functions (e.g., acyl and alkyl derivatives) and modifications of the double bonds (e.g., the perhydrogenated and hydroxylated derivatives of the mentioned acids).

The mixing ratio of component (a) to component (b) is preferably between 10,000:1 and 1:10,000, more preferably between 1000:1 and 1:1000, and even more preferably between 100:1 and 1:100.

In a preferred embodiment of the method according to the invention, the anti-microbial composition contains:

(a1) an aromatic GRAS flavor alcohol as a necessary component; and optionally (a2) one or more further GRAS flavor alcohols or their derivatives; and (b1) one or more polyphenol compounds; and/or (b2) one or more GRAS acids or their derivatives.

Suitable aromatic GRAS flavor alcohols according to the present invention include benzyl alcohol, 1- and 2-phenylethanol, cinnamic alcohol, hydrocinnamic alcohol, and 1-phenyl-1-propanol. Particularly preferred is benzyl alcohol. It is particularly preferred for the further GRAS flavor alcohol (a2) to be a hydrophilic GRAS flavor alcohol, and/or for the GRAS acids (b2) to be a hydrophilic GRAS acid. Hydrophilic GRAS flavor alcohols according to the present invention include monohydric or polyhydric alcohols containing from 2 to 7 carbon atoms, 1-Propanol, glycerol, propylene glycol and acetoin being particularly preferred. The hydrophilic GRAS acid includes organic acids containing from 2 to 10 carbon atoms, wherein acetic acid, aconitic acid, formic acid, malic acid, lactic acid, phenylacetic acid, citric acid, mandelic acid, tartaric acid, fumaric acid, tannic acid, hydrocinnamic acid and their physiologically acceptable salts are particularly preferred.

Suitable amounts of components (a1), (a2), (b1) and (b2) are:

from 0.1 to 99% by weight, preferably from 0.1 to 75% by weight, of component (a1);

from 0 to 99.8% by weight, preferably from 0.01 to 99% by weight, of component (a2);

from 0 to 25% by weight, preferably from 0.01 to 10% by weight, of component (b1); and/or from 0 to 70% by weight, preferably from 0.01 to 30% by weight, of component (b2).

Either component (a1) or (a2) can be the main component. In the former case, the composition contains at least 20%, preferably from 40 to 99%, by weight of aromatic GRAS alcohol, preferably benzyl alcohol. In the second case, it contains at least 40%, preferably from 50 to 99%, by weight of hydrophilic GRAS flavor alcohol, preferably propylene glycol. Particularly preferred according to the present invention is a composition which contains from 0.1 to 10% by weight of benzyl alcohol, at least 75% by weight of propylene glycol, and at least 0.01% by weight of (b1) and/or (b2).

The antimicrobial composition may further contain the following components (c) to (h), which are also flavoring agents recognized in the FEMA/FDA GRAS Flavour Substances List as GRAS (generally recognized as safe in food) 3-15 Nos. 2001-3815 (as of 1997).

As component (c), the following phenol compounds may be employed:

thymol, methyleugenol, acetyleugenol, safrol, eugenol, isoeugenol, anethole, phenol, methylchavicol (estragol; 3-(4-methoxyphenyl)-1-propene), carvacrol, á-bisabolol, formesol, anisole (methoxybenzene), propenylguaethol (5-propenyl-2-ethoxyphenol) and their derivatives.

As GRAS esters (component (d)), allicin and the following acetates may be used:

iso-amyl acetate (3-methyl-1-butyl acetate), benzyl acetate, benzylphenyl acetate, n-butyl acetate, cinnamyl acetate (3-phenylpropenyl acetate), citronellyl acetate, ethyl acetate (acetic ester), eugenol acetate (acetyleugenol), geranyl acetate, hexyl acetate (hexanyl ethanoate), hydrocinnamyl acetate (3-phenylpropyl acetate), linalyl acetate, octyl acetate, phenylethyl acetate, terpinyl acetate, triacetin (glyceryl triacetate), potassium acetate, sodium acetate, calcium acetate.

Further suitable esters are the ester derivatives of the above defined acids (component (b2)).

As terpenes (component (e)), there may be used, for example, camphor, limonene and â-caryophyllene.

The acetals (component (f)) which can be used include, e.g., acetal, acetaldehyde dibutyl acetal, acetaldehyde dipropyl acetal, acetaldehyde phenethyl propyl acetal, cinnamic aldehyde ethylene glycol acetal, decanal dimethyl acetal, heptanal dimethyl acetal, heptanal glyceryl acetal and benzaldehyde propylene glycol acetal.

As aldehydes (component (g)), there may be used, e.g., acetaldehyde, anisaldehyde, benzaldehyde, iso-butyl aldehyde (methyl-1-propanal), citral, citronellal, n-caprylic aldehyde (n-decanal), ethylvanillin, furfural, heliotropin (piperonal), heptyl aldehyde (heptanal), hexyl aldehyde (hexanal), 2-hexenal (á-propylacrolein), hydrocinnamic aldehyde (3-phenyl-1-propanal), lauryl aldehyde (do-decanal), nonyl aldehyde (n-nonanal), octyl aldehyde (n-octanal), phenylacetaldehyde (1-oxo-2-phenylethane), propionaldehyde (propanal), vanillin, cinnamic aldehyde (3-phenylpropenal), perillaldehyde and cuminaldehyde.

The following essential oils and/or alcoholic or glycolic extracts or extracts obtained by $CO_2$ high-pressure processes from the mentioned plants (component (h)) can also be employed according to the invention:

(h1) oils or extracts having a high content of alcohols: melissa, coriander, cardamon, eucalyptus;

(h2) oils or extracts having a high content of aldehydes: Eucalyptus citriodora, cinnamon, lemon, lemon grass, melissa, citronella, lime, orange;

(h3) oils or extracts having a high content of phenols: *origanum*, thyme, rosemary, orange, clove, fennel, camphor, mandarin, anise, cascarilla, estragon and pimento;

(h4) oils or extracts having a high content of acetates: lavender;

(h5) oils or extracts having a high content of esters: mustard, onion, garlic;

(h6) oils or extracts having a high content of terpenes: pepper, bitter orange, caraway, dill, lemon, peppermint, nutmeg.

The proportion of components (c) to (h) in the antimicrobial composition is preferably smaller than or equal to 25% by weight, more preferably within a range of from 0.001 to 9% by weight. Preferred among the further GRAS flavoring agents are the phenols (c) and essential oils (h).

Particularly preferred according to the present invention are antimicrobial compositions in which the antimicrobially active component exclusively consists of GRAS flavoring agents, i.e., which does not contain any "derivatives" of the GRAS flavoring agents. As an example of such a composition, there may be mentioned a mixture of benzyl alcohol, one or two of the above mentioned GRAS flavor alcohols (a2) and tannin. Such a mixture preferably contains from 0.1 to 99.9% by weight, more preferably from 0.1 to 20% by weight, of benzyl alcohol, and from 0.01 to 10% by weight of tannin. Another example of a preferred composition is a mixture of 2 alcohols, a polyphenol (especially tannin) and an essential oil (especially a phenolic essential oil, component (h3)).

In addition to components (a) to (h), further compounds (i), such as alcohols (i1), emulsifiers (i2), stabilizers (i3), antioxidants (i4), preservatives (i5), solvents (i6), carriers (i7), water (i8), etc., may additionally be employed. The proportion of components (i) in the antimicrobial composition may be up to 95% by weight, is preferably smaller than 10% by weight, and is more preferably within a range of from 0.1 to 5% by weight.

According to the invention, the alcohols (i1) are monohydric or polyhydric alcohols having from 2 to 10 carbon atoms, preferably having from 2 to 7 carbon atoms, not including the GRAS alcohols (a). Preferably, the GRAS flavor alcohols (a) and further alcohols (i1) are employed in such amounts that their mixing ratio is between 1000:1 and 1:1000, especially between 100:1 and 1:100, and more preferably between 10:1 and 1:10.

In the method according to the invention, it is particularly preferred to use systems which exclusively consist of GRAS flavoring agents, especially when the treated air will contact food, beverages or packages in food-processing plants, since this also avoids the risk of contamination of the treated foodstuffs with non-GRAS compounds.

The distributing/atomizing of the antimicrobial composition is effected by commercially available two-fluid nozzles or evaporation techniques. It has been found particularly advantageous to use a method described in PCT/EP 00/02992 in which the antimicrobial composition, also referred to as air treatment agent in the following, is introduced into the air in a liquid phase and evaporated, wherein the proportion of treatment agent in the air per $m^3$ of air is between 0.1 and 0.00001 ml, preferably between 0.01 and 0.0001 ml.

This method preferably comprises the following steps:

feeding of the air treatment agent from a storage chamber into a vortexing chamber through which air is flowing;

adjusting the supplied amount of air and the supplied amount of air treatment agent to achieve a proportion of treatment agent of between 0.1 and 0.00001 ml, preferably between 0.01 and 0.0001 ml, per $m^3$ of air per hour; and introducing the mixture of air and vaporized air treatment agent into a room to be treated.

When such low amounts of air treatment agent per $m^3$ of air are used, precipitation of the air treatment agent can no longer be detected. Therefore, the method may also be employed for the treatment of air in storage rooms for food. Also in waiting rooms or apartments of allergic people and the like, the use of this method is particularly advantageous because an annoying precipitate on cool windows or the like will not occur.

For a proportion of air treatment agent of as low as 1 ppt (parts per trillion, volume base), a significant antimicrobial activity was detected. Thus, at 15 ppt (vol.), an average germ reduction of 70% could be detected in an experiment.

The proportion of air treatment agent in the ambient air, which is adjusted by the method (1) according to the invention, is usually <10 ppb (parts per billion, volume base), preferably #100 ppt (vol.), more preferably #10 ppt (vol.). Already such low amounts of air treatment agent can achieve a germ reduction which corresponds to clean-room conditions. However, one precondition is that the water content of the antimicrobial composition (especially for those compositions which mainly consist of hydrophilic GRAS flavoring agents, e.g., propylene glycol) be less than 35% by weight, preferably from 5 to 25% by weight.

Preferably, in the method for introducing the air treatment agent into the air, the air treatment agent is first supplied from a storage chamber to a vortexing chamber through which air is flowing. The amount of air supplied to the vortexing chamber and the amount of air treatment agent supplied to the vortexing chamber are adjusted to provide a proportion of air treatment agent of between 0.1 and 0.00001 ml, preferably between 0.01 and 0.0001 ml per $m^3$ of air per hour. In a continuous method (like an air-conditioning system), this produces a permanent concentration of from 5 to 10 ppb of air treatment agent in the ambient air. Subsequently, the mixture of air and vaporized air treatment agent is introduced into the space to be treated.

The evaporation of the air treatment agent occurs without the supply of heat. Exclusively due to the vortexing of the air treatment agent, uptake of the low amount of air treatment agent by the air is achieved. The amount of air treatment agent dragged away by the current of air is so low that an aerosol is not formed. The vortexing of the air treatment agent in the vortexing chamber generates a large number of air bubbles. This increases the surface of the air treatment agent in such a way that low amounts of air treatment agent are taken up by the current of air.

The amount of air supplied to the vortexing chamber and the amount of air treatment agent supplied to the vortexing chamber can be established empirically. Care is to be taken that the speed of the current of air is not so high that droplets of air treatment agent are dragged away. On the other hand, too low an amount of air treatment agent contained in the vortexing chamber causes that insufficient vortexing occurs. It has been found that particularly good results can be achieved at a ratio of the amount of air supplied to the amount of air treatment agent supplied of between 45%/55% and 30%/70%. Preferably, this ratio is between 42%/58% and 35%/65%.

Preferably, before being introduced into the space to be treated, the mixture of air and air treatment agent is conducted through an intermediate chamber which is separated from the vortexing chamber by a retaining disk. The function of the intermediate chamber is to allow excess air treatment agent in the air to condensate out. This is supported by the retaining disk, which preferably has fine apertures or is designed as a fine-pore membrane. Thus, the intermediate chamber serves as a drop separator. This ensures that no aerosol will get into the space to be treated. In the mixture of air and vaporized air treatment agent flowing into the space to be treated, a precipitate cannot be detected with conventional methods.

Since the amount of air treatment agent introduced into the vortexing chamber is significantly higher than the proportion of treatment agent contained in the mixture of air and air treatment agent, excess air treatment agent is discharged from the vortexing chamber. Preferably, the air treatment agent is recirculated into the storage chamber. From here, it can be reintroduced into the vortexing chamber immediately.

Figure 6:
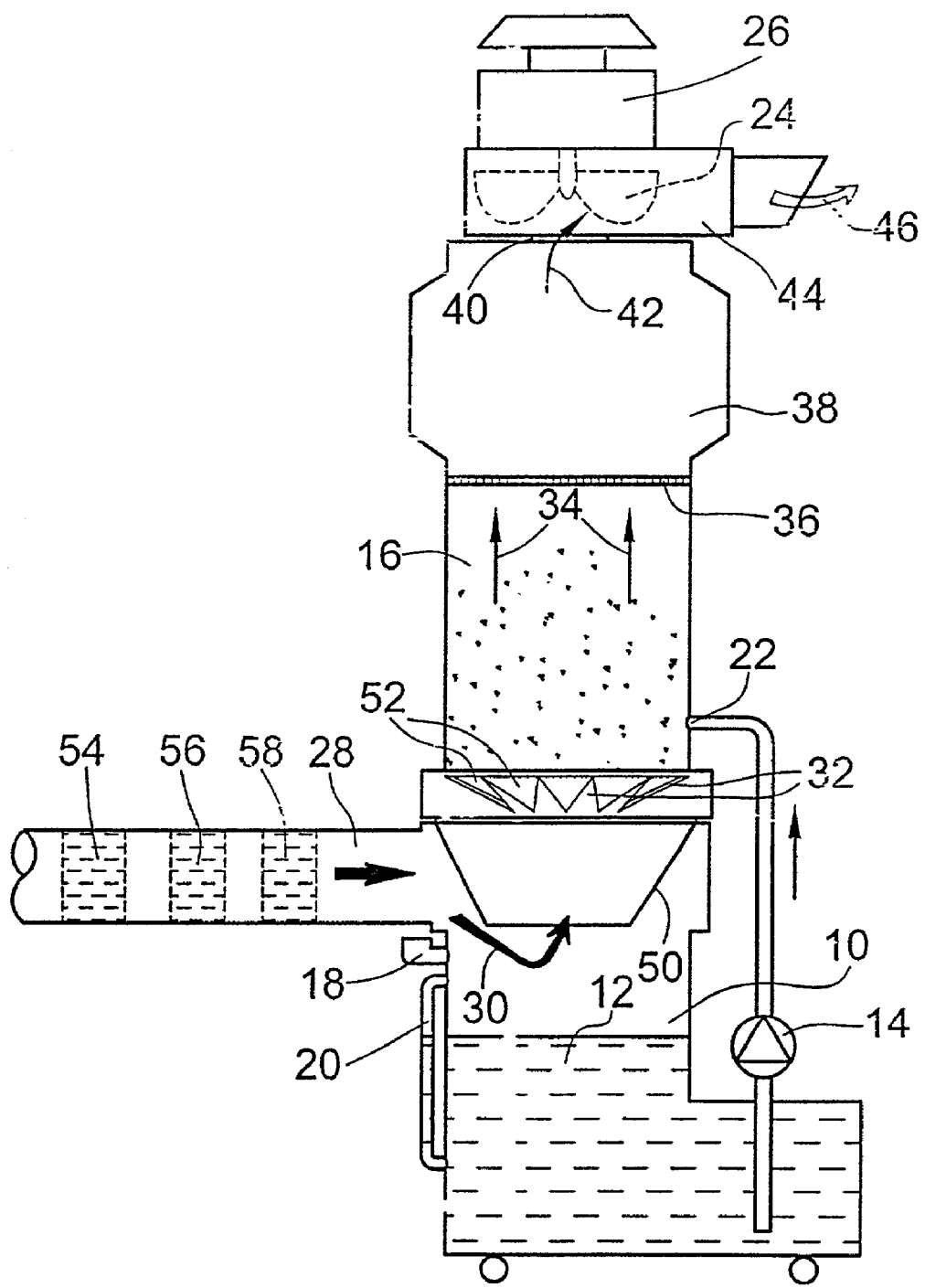
Figure 7:
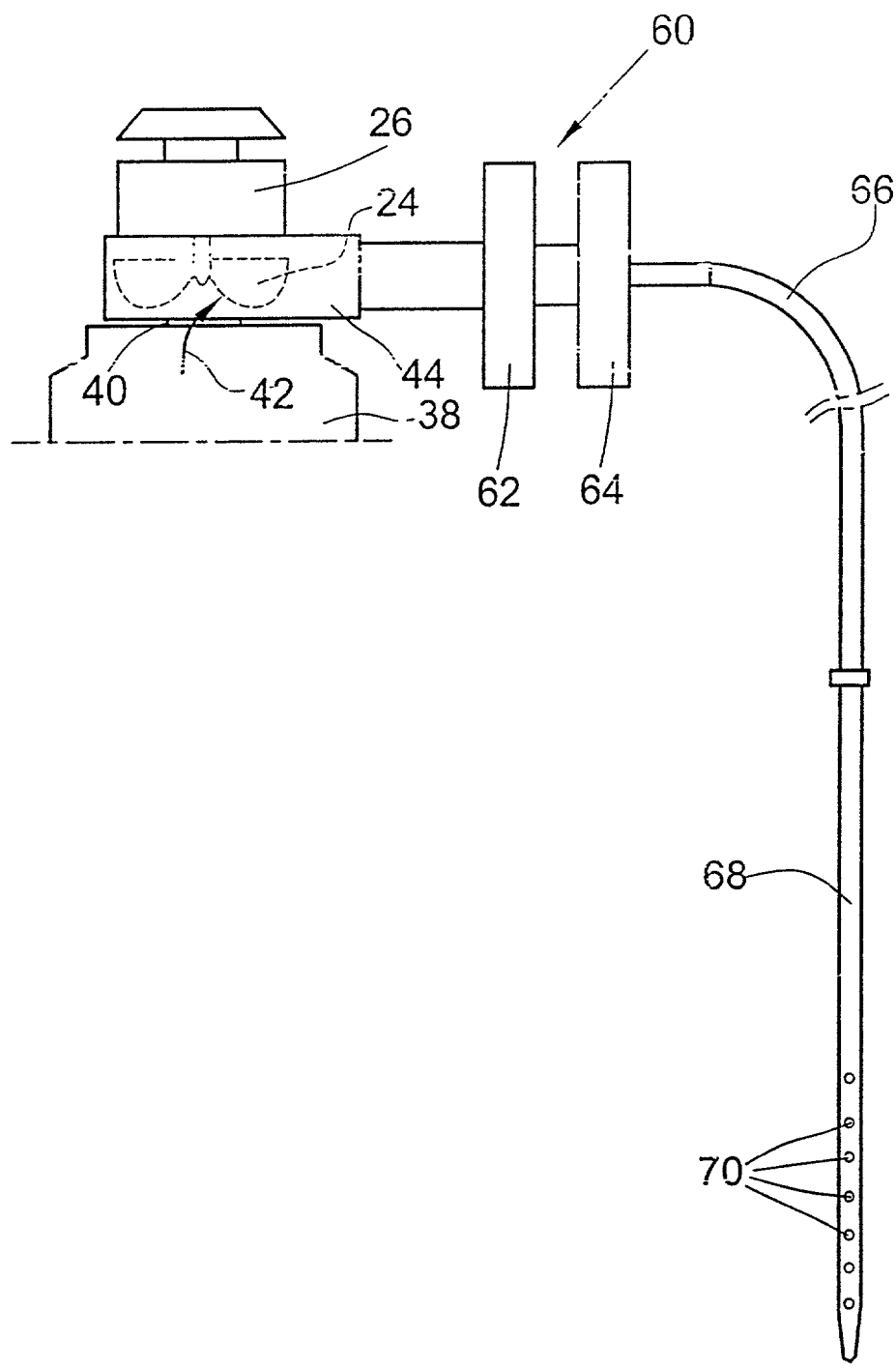

Devices designated for this purpose, such as a bubbler means, which applies disinfectant to the air in a superfine distribution and with the lowest possible dose, and a device to be applied especially to the package are depicted in the accompanying Figures. Particularly preferred is a device described in PCT/EP 00/02992 and shown in FIGS. 6 and 7 in the present application which is suitable, in particular, for the disinfection of air and comprises a storage chamber, a vortexing chamber and a means for generating a current of air. The storage chamber contains a liquid air treatment agent. The liquid air treatment agent is supplied to the vortexing chamber, for example, using a pump. Depending on the configuration of the device, the means for generating a current of air can be a fan sucking the mixture out of the vortexing chamber, or a fan blowing air into the vortexing chamber. The fan is arranged in such a way that a current of air is generated in the vortexing chamber due to which the vortexing of the liquid treatment agent is effected. Due to the vortexing of the air treatment agent, the air takes up a small amount of air treatment agent, so that a mixture of air and vaporized air treatment agent exits from the vortexing chamber.

The device is suitable for performing the method according to the invention, so that the mixture of air and vaporized air treatment agent exiting from the device has a proportion of air treatment agent per $m^3$ of air per hour of between 0.1 and 0.00001 ml, preferably between 0.01 and 0.0001 ml. Depending on the kind of treatment agent, the proportion of the treatment agent in the air can be adjusted by the ratio of the amount of air supplied to the amount of treatment agent supplied to the vortexing chamber. It has been found that such a low proportion of treatment agent can be achieved at a ratio of the amount of air to the amount of treatment agent of between 45%/55% and 30%/70%, preferably between 42%/58% and 35%/65%.

Preferably, the vortexing chamber has air inlets in the bottom region through which air flows into the vortexing chamber. Further, excess air treatment agent can drain from the vortexing chamber through the air inlets in a direction opposite to that of the air flow.

In experiments with an air disinfectant, a proportion of treatment agent of 0.01 ml per $m^3$ of air was achieved at an air flow rate of about 1100 $m^3$ per hour. Thus, with the above mentioned ratios between the air and the treatment agent, a very low proportion of air treatment agent is taken up by the air, and a major portion of the air treatment agent is discharged from the vortexing chamber. This is a surprising effect, because a very low proportion of air treatment agent is taken up by the air due to the vortexing despite of the very large amount of air treatment agent present in the vortexing chamber. To introduce such low amounts of air treatment agent into the air is not possible with spraying techniques or with thermal evaporation. In particular, it is not possible when known devices are operated without pulsing. However, in the device according to the invention, the above result was achieved without any pulsing.

In order to ensure that actually no precipitating aerosol escapes from the device, an intermediate chamber is provided downstream of the vortexing chamber. Between the intermediate chamber and the vortexing chamber, a retaining disk is provided. Any droplets of air treatment agent dragged away by the current of air are retained by the retaining disk, on the one hand, and will condensate out in the intermediate chamber, on the other hand.

Preferably, filters are inserted upstream of the air inlets of the vortexing chamber in order to supply air to the device which is as much as possible free of germs, particles and bacteria. For this purpose, a particle filter and/or a bacterial filter and/or a moisture filter are provided.

Advantageously, the device is coupled to an air conditioning system, so that a distribution of the air treatment agent throughout the space is ensured by the air conditioning system.

In another embodiment, a pressure generating means is provided downstream of the device to increase the pressure of the exiting mixture of air and vaporized air treatment agent. Such a device can be used, for example, to ensure that the mixture is blown also into the corners of a room.

To a device with a pressure generating means connected thereto, a lance with air outlets can be connected. The lance can be inserted into food packages in order to introduce the air treatment agent into the package.

With the device described here, the above defined antimicrobial compositions, in particular, can be released into the air. In the following, FIGS. 6 and 7 will be described in some detail.

A storage chamber 10 contains air treatment agent 12. The air treatment agent 12 is pumped from the storage chamber 10 into a vortexing chamber 16 using a pump 14. Further, the storage chamber 10 is provided with a filler neck 18 for replenishing air treatment agent 12 and with a level indicator 20 having the shape of a transparent tube.

The air treatment agent 12 pumped from the storage chamber 10 into the vortexing chamber 16 is supplied to the vortexing chamber 16 through an inlet 22. Depending on the pump pressure and the size of the inlet 22, the air treatment agent 12 is injected into the vortexing chamber 16 at different pressures. This injection of the air treatment agent 12 can increase the vortexing effect in the vortexing chamber 16.

Using a fan 24 serving as a means for generating a current of air and driven by a motor 26, air is sucked through an air supply duct 28 into the upper region of the storage chamber 10. From there, the air enters the vortexing chamber 16 in the direction of arrow 30 through air inlets 32 provided in the bottom region of the vortexing chamber 16. From there, the air current enters an intermediate chamber 38 in the direction of arrows 34 through a retaining disk 36. From the intermediate chamber 38, the mixture of air and air treatment agent enters a fan chamber 44 through a tubular connection piece 40 in the direction of arrow 42, and from there, it enters the space to be treated in the direction of arrow 46.

The air inlets 32 provided in the bottom region of the vortexing chamber 16 are radially arranged slots through which the air enters the vortexing chamber 16. Since the amount of air treatment agent 12 supplied to the vortexing chamber 16 is higher than the proportion of air treatment agent in the mixture exiting the device, a major portion of the air treatment agent 12 must be recirculated from the vortexing chamber 16 into storage chamber 10. In the embodiment shown, the excess air treatment agent 12 flows through the slot-shaped air inlets 32 back into the storage chamber 12. For this purpose, the bottom region of the vortexing chamber 16 in which the air inlets 32 are provided has a funnel-shaped design. In order to ensure a well-aimed backflow of the excess air treatment agent, a funnel 50 is provided in the upper region of the storage chamber 10. Further, the funnel 50 prevents air treatment agent 12 from getting into the air supply duct 28.

The slot width of the air inlets 32 can be adjusted because the bottom region consists of individual triangular segments 52 whose inclination angle can be adjusted. The steeper the segments 52 are arranged, the larger are the slot-shaped air inlets 32.

The mixture of air and air treatment agent exiting from the vortexing chamber 16 is conducted through the retaining disk 36 into the intermediate chamber 38. The retaining disk 36 has apertures of low diameter or consists of a membrane having a fine porosity. The retaining disk 36 retains any droplets of air treatment agent dragged away by the current of air, so that only vaporized air treatment agent gets into the intermediate chamber 38, if possible.

The intermediate chamber 38 is provided as an additional safeguard. It ensures that any air treatment agent present in the mixture of air and air treatment agent which is not in a vaporized form will condensate out in the intermediate chamber 38. The portion of the air treatment agent which condensates out on the walls of the intermediate chamber 38 flows through the retaining disk 36 back into the vortexing chamber 16. From the intermediate chamber 38, a mixture of air and vaporized air treatment agent exclusively enters the fan chamber 44 along the arrow 42. The mixture entering the fan chamber 44 does not contain any more aerosol, so that the small amount of air treatment agent present in the mixture can no longer be detected as a precipitate.

In the air supply duct 28, a particle filter 54, especially a pollen filter, a bacterial filter 56 and a moisture filter 58, is provided for filtering the air sucked in. The moisture filter 58 withdraws the moisture from the air sucked in because the air treatment agents used are often hygroscopic.

To the fan chamber 44, a pressure generating means 60 (FIG. 7) can be connected. In the example shown, this is a two-step pressure generating means having a first pressure generating step 62 and a second pressure generating step 64. After the pressure generating means 60, the mixture of air and air treatment agent is introduced into a flexible tube 66 under increased pressure. To the flexible tube 66, a lance 68 with outlets 70 is connected. The lance 68 can be inserted into food packages to fill them with the mixture of air and air treatment agent.

When an air disinfectant is discharged by the device according to the invention, it can be introduced into packages of rolls and the like instead of nitrogen. The air disinfectant causes death of the mold germs present on the rolls. This ensures that the rolls cannot start to mold even when there are small apertures, which frequently occur in the welding seams of the package. This is not the case when nitrogen or the like is used, because nitrogen only suppresses the formation of mold. This means that the rolls start to mold as soon as fresh air gets into the package. When an air disinfectant is used, mold germs must also intrude into the package in addition to fresh air. Generally, it is not possible for them to intrude through the very small apertures in the welding seams. The use of air disinfectants in packages significantly reduces the risk of molding of the food contained.

The atomizing/distributing is generally effected in such a way that the concentration of the antimicrobial composition is from 0.001 to 1 ml per $m^3$ of air, especially from 0.01 to 0.1 ml per $m^3$ of air. With exchanging air systems in which an hourly recirculation is effected, the method is to be adjusted to provide a dosage of from 0.001 to 1 ml per $m^3$ per hour, especially from 0.02 to 0.1 ml per $m^3$ per hour.

In experimental examples, it could be shown that a reduction factor $R_f$ of 5 to 3 powers of ten can be achieved by the distributing or atomizing of the antimicrobial composition according to the invention, i.e., a reduction of the germs per $m^3$ of air from 10,000 to 0 is possible.

Thus, the present method is suitable for the disinfection of the air in private households, offices and public buildings as well as in food-processing plants, transport devices, cooling, air-conditioning and other aeration fields. In the latter, a significantly higher stability of the food is achieved by the disinfection of the ambient air (e.g., in the packaging of the food).

The present invention will be illustrated in more detail by the following Examples.

EXAMPLES

Apparatus employed: For the Examples described below, the devices depicted in FIGS. 1 to 4, 6 and 7 were used.

FIG. 1: Air DOA (disinfection of air) bubbler

Autonomous, permanently installed or mobile bubbler unit with incorporated exhaust fan and pump. Air quantity: 2 to 1600 $m^3$/h (or larger).

Principle of function: Bubbler with floating DOA fluidized bed

Air with counter-current DOA agent. The DOA agent is caused to float in a chamber with a highly reduced pressure. This generates an equilibrium between the reduced pressure of the air and the DOA average weight. The air is distributed over the entire DOA surface and rises through the DOA bed in the form of microscopically sized bubbles. The air bubbles form a very large contact area between the gas and liquid. The air pressure and dwelling time are in a well-balanced proportion. The DOA agent is transported along with the air in a corresponding dosage.

Fan: The exhaust radial fan is always positioned in the clean air zone and may also be installed externally.

Bubbler: The washer consists of:
absorption liquid container
washing chamber
drying chamber
fan Legend for FIG. 1:

1) air suction piece with/without microfilter

Figure 2A:
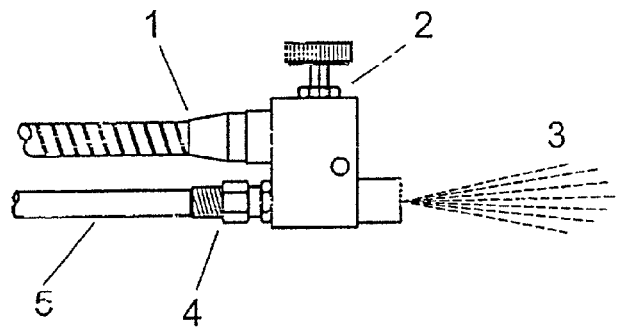
Figure 2B:
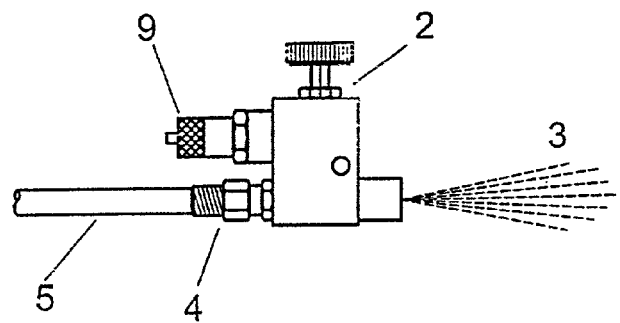
Figures 2A, 2B, 2C:
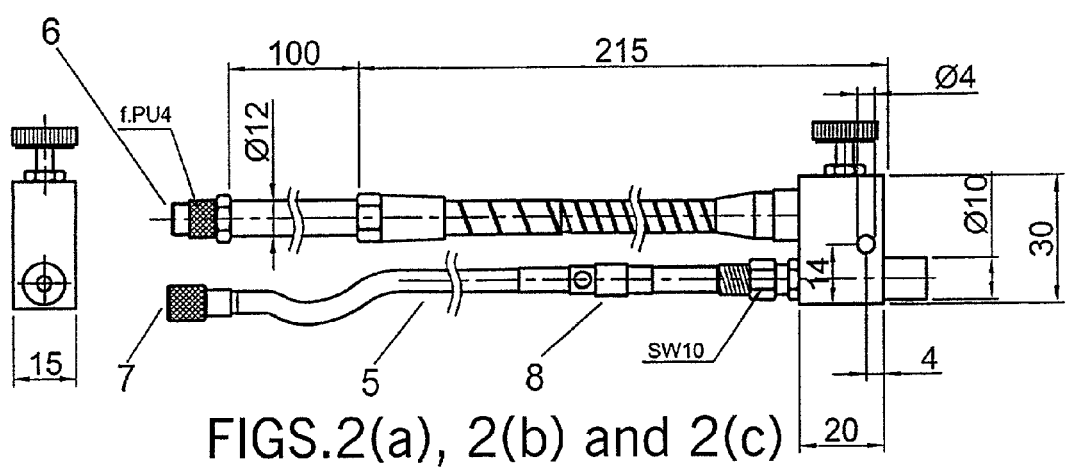

2) DOA agent supply 3) e.g., pump 15 $m^3$/h motor 220/380 V; 2800 rpm; 1.1 kW 5) dosing unit (electric) quantity/air ratio DOA agent dosing 0.02 ml to 0.1 ml/$m^3$ (h) dosage 6) DOA agent 7) DOA agent 9) washing chamber 10) dryer 12) fan 1200/1800 $m^3$/h motor 220/380 V; 2800 rpm; 1.1 kW 15) exhaust piece, e.g., diameter 200 mm FIGS. 2A, 2B and 2C: DOA atomizer low pressure system (for thin liquids)

For atomizing thin oils and liquids with a well-aimed field of activity.

The atomizer responds already from a pressure of 2 bar gauge.

With the flexible metal tube, the atomizer can be rotated and turned as desired, and attached at any place using the magnetic holder.

Function: When compressed air is applied, atomizing occurs immediately (a built-in check valve prevents the liquid level in the flexible tube from dropping). The atomizer works permanently, or intermittently with the automatic blowing device, but always in well-dosed quantities. In the center of the air jet, the liquid is economically and cleanly supplied. Through the air and liquid throttle, the amount of air and liquid can be finely adjusted. The atomizer can be continuously adjusted at a spraying angle of from 10E to 30E.

Legend for FIGS. 2A, 2B and 2C:

1) flexible metal tube, nickel-coated 2) air throttle 3) spraying angle 10E-30E 4) liquid throttle 5) PVC flexible tube 1 m 6) connection for PK4

7) screen valve 8) check valve 9) connection for compressed air 10) throttle ball (not visible)

Figure 3:
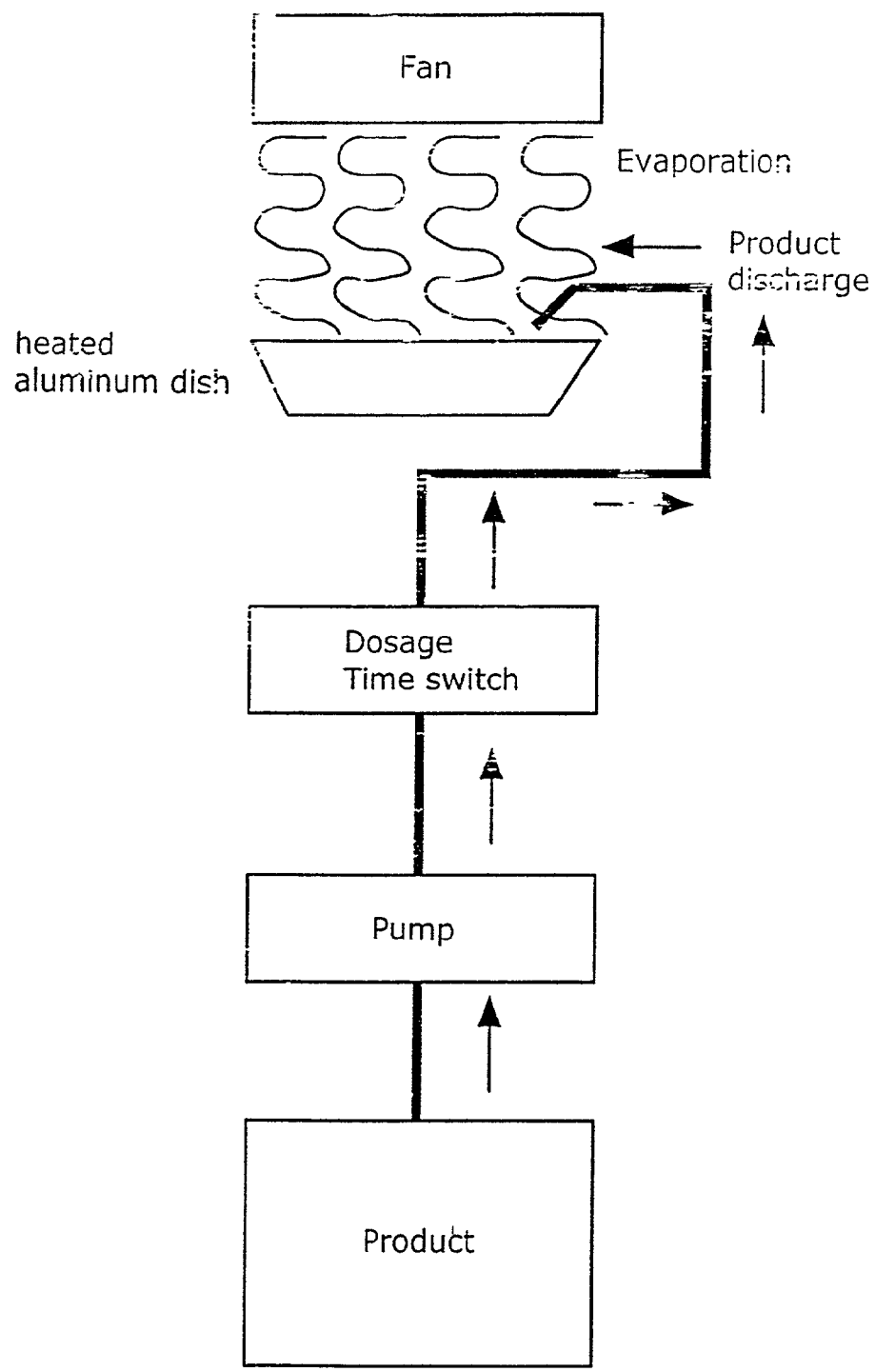

FIG. 3: DOA evaporation system

Figure 4:
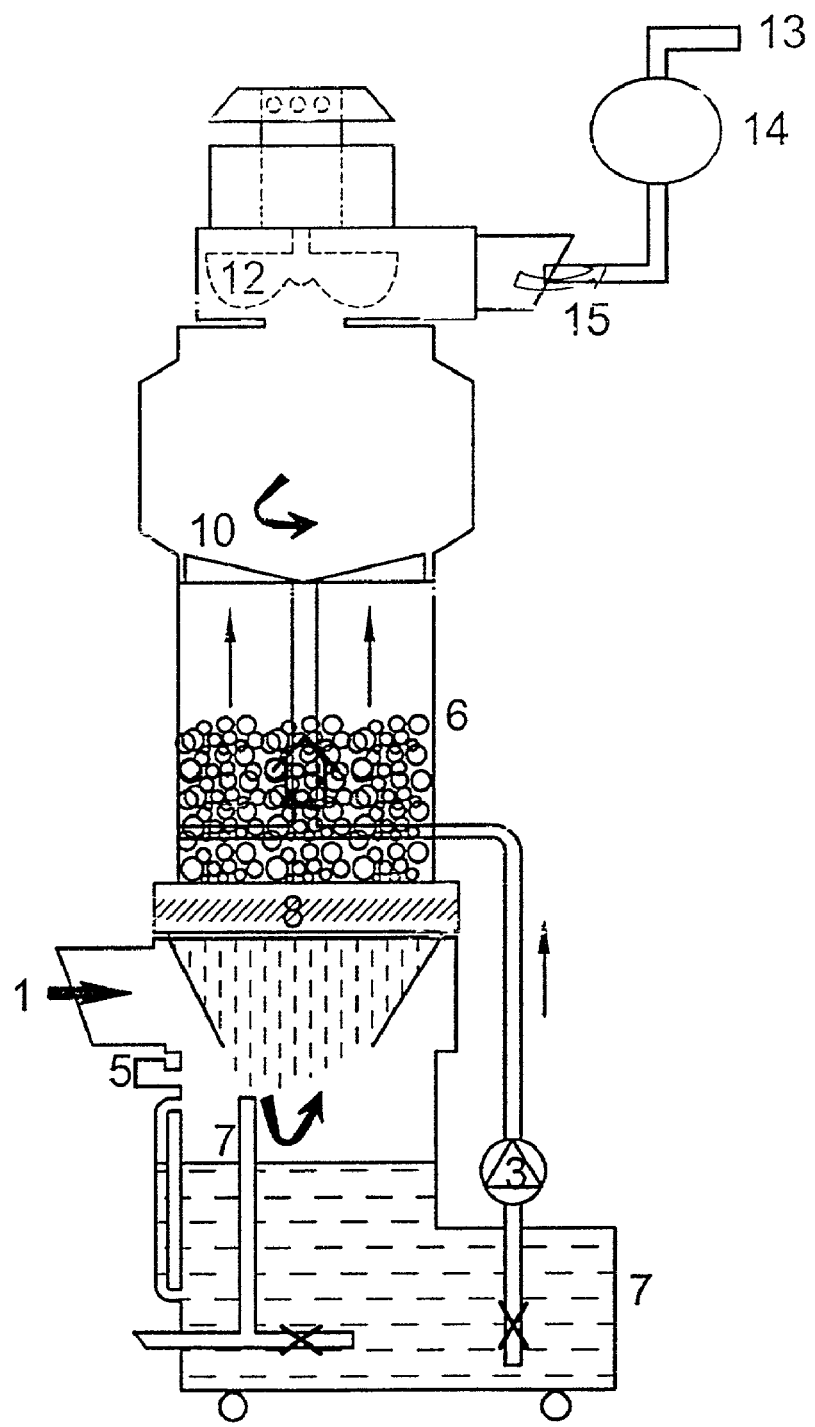

FIG. 4: DOA disinfection in a package with bubbler

Fan: The exhaust radial fan is always positioned in the clean air zone and may also be installed externally.

Legend for FIG. 4:

1) air and/or $CO_2$/or nitrogen or the like suction piece with/without microfilter 2) DOA agent supply 3) pump 15 $m^3$/h motor 220/380 V; 2800 rpm; 1.1 kW 5) dosing unit (electric) quantity/air ratio DOA agent dosing 0.02 ml to 0.1 ml/$m^3$ (h) dosage 6) DOA agent 7) DOA agent 9) washing chamber 10) dryer 12) fan 1200/1800 $m^3$/h motor 220/380 V; 2800 rpm; 1.1 kW 13) discharge into package (e.g., via lance)

14) pressure reservoir (about 2 to 8 bar compressed) consisting of air and $CO_2$ and $N_2$ and DOA agent with low moisture 15) exhaust piece, e.g., diameter 200 mm Disinfectant: In the following Examples, a disinfectant composition consisting of 5.5% by weight of polyphenol (e.g., tannin), 10.3% by weight of benzyl alcohol, 4.2% by weight of essential oil (phenolic) and 80.0% by weight of propylene glycol is used (also referred to as "DOA agent" or "DOAA" in the following)

Example 1

Examination of the Disinfection of Air Using the Device Represented in FIG. 1

| | |
|---|---|
| Project: | Activity examination of DOA in combination with dosage by bubbler (prototype) system (FIG. 1) |
| Sample type: | Gelatin filter from air-borne germ collector Satorius MD-8 |
| Examination method: | BLA 9420/TRBA 430, indirect method |
| Sample parameters | |
| Measuring time: | 5 min |
| Volume flow: | 8 $m^3$/h |
| Sampling volume: | 666.671 |
| Dosage: | 0.02 ml/$m^3$ of DOA agent |
| Total germ number (cfu): | Mixture of molds and yeasts (*Penicillium commune*, *Cladosporium*, *Aspergillus niger*, *Saccharomyces cerevisiae*) |

The results are summarized in Table 1.

TABLE 1

| Original No. | Sampling place (day) | Number of germs |
|---|---|---|
| 99669-12 | Test chamber, zero value, 0 | 10,400 cfu/$m^3$ |
| 99669-13 | Test chamber, zero value, 0 | 11,150 cfu/$m^3$ |
| 99669-14 | Test chamber, 10:45, 1 | 50 cfu/$m^3$ |
| 99669-15 | Test chamber, 10:55, 1 | 0 cfu/$m^3$ |
| 99669-16 | Tesi chamber, 18:35, 1 | 0 cfu/$m^3$ |
| 99669-17 | Test chamber, 18:40, 1 | 50 cfu/$m^3$ |

TABLE 1-continued

| Original No. | Sampling place (day) | Number of germs |
|---|---|---|
| 99669-18 | Test chamber, 10:15, 2 | 0 cfu/m$^3$ |
| 99669-19 | Test chamber, 10:25, 2 | 0 cfu/m$^3$ |
| 99669-20 | Test chamber, 19:10, 2 | 0 cfu/m$^3$ |
| 99669-21 | Test chamber, 8:50, 5 | 0 cfu/m$^3$ |
| 99669-22 | Test chamber, 9:00, 5 | 0 cfu/m$^3$ |
| 99669-23 | Test chamber, 10:15, 6 | 0 cfu/m$^3$ |
| 99669-24 | Test chamber, 10:20, 6 | 0 cfu/m$^3$ |
| 99669-25 | Test chamber, 18:40, 6 | 0 cfu/m$^3$ |
| 99669-26 | Test chamber, 18:50, 6 | 0 cfu/m$^3$ |
| Handling BL | 18:40, 6 | 0 cfu/m$^3$ |

By introducing germs (molds), total germ number corresponds to 10,000 germs (cfu)/m$^3$ of air and its bacteriological zero value.

In the control, after introducing (fine distribution of the DOA agents by bubbler system (see technical function)) the DOA agent, a germ load in the air could no longer be detected mostly after the 1st to 6th day.

Example 2

Verification of Applications for the Disinfection of Air Using the Device Represented in FIG. 2.

| | |
|---|---|
| Application: | Nebulizing in the ambient air for reducing the number of germs |
| Problem: | Generally high number of germs including pathogenic bacteria (Gram-positive and Gram-negative), *Bacillus* spec. |
| Dosage: | 0.02 to 0.10 ml of DOA agent per cm$^3$ of air/h |

Performance

| Simulation of the following room climate: | |
|---|---|
| Temperature: | about 25° C. |
| Rel. humidity: | about 55% |

Discontinuous recirculation of air using appropriate equipment (atomizer low pressure (AL) two-fluid nozzle system); deliberate contamination with *Bacillus subtilis, Pseudomonas fluorescens* and *Staphylococcus aureus* (10$^2$ to 10$^3$) and discontinuous spraying of the room with DOA device using AL head nozzle spraying technique (every 200 s, spraying for 5 s)

Object/result: Reduction of the germ content of the ambient air (bacteriology: total number of colonies, *Pseudomonas fluorescens* as a guide germ for *Legionella* spp., *Staphylococcus aureus, Bacillus subtilis*)

Sampling (RCS air-borne germ measurements and sedimentation plates). Before inoculation, after inoculation immediately before use.

Daily, until a reduction can no longer be established (once to twice daily sedimentation plates in two places, 1×RCS).

Evaluation

| | |
|---|---|
| Testing region: | Room without air conditioning system, 32.8 m$^3$ |
| Preliminary result: | RCS device<br>total germ number: 380/m$^3$ |

| | |
|---|---|
| Performance: | Artificial loading of the ambient air with *Bacillus subtilis, Pseudomonas fluorescens* and *Staphylococcus aureus*. Measurements were performed predominantly in the morning and in part in the evening after a fan had been switched on for 4 min. |
| Result: | See following Table 2 |
| Comment: | After the bacterial suspension had been introduced, a dramatic germ reduction could be detected already when DOA nebulization was performed after one day. Already after one day, *Pseudomonas* or *Bacillus subtilis* could no longer be detected in the air. Also, after about 30 hours, *Staphylococcus* germs could no longer be detected in the air. In practice, this means that the air can be permanently freed from *Bacillus subtilis* and *Staphylococcus aureus* as well as *Pseudomonas* spec. and thus also *Legionella* spp. by application of DOA. |

TABLE 2

Sedimentation plates (exposition time 30 min)

| | | front part of the room | | | rear part of the room | | |
|---|---|---|---|---|---|---|---|
| Control day | RCS/m$^3$ TGN | TGN | Staph. aureus | Pseudo-monas | TGN | Staph. aureus | Pseudo-monas |
| 0 morning | 8,600 | 1,300 | 1,900 | 640 | 1,560 | 2,400 | 570 |
| 1 morning | 240* | 16 | 1 | <1 | 10 | <1 | <1 |
| evening | 205* | 9 | <1 | <1 | 12 | <1 | <1 |
| 2 morning | 105* | 1 | <1 | <1 | 3 | <1 | <1 |
| evening | 135* | 3 | <1 | <1 | 3 | <1 | <1 |
| 3 morning | 15* | 1 | <1 | <1 | 1 | <1 | <1 |
| 4 morning | 15*[1] | 1 | <1 | <1 | <1 | <1 | <1 |
| 5 morning | 10*[1] | 2* | <1 | <1 | 4* | <1 | <1 |
| evening | 14*[1] | 1* | <1 | <1 | 2* | <1 | <1 |
| 6 morning | 40*[1] | 5* | <1 | <1 | 6* | <1 | <1 |
| 7 morning | 35*[1] | 4* | <1 | <1 | 3* | <1 | <1 |

\* = no *Bacillus subtilis*, no *Pseudomonas* spec., no *Staph. aureus*
\*[1] = predominantly molds

| | |
|---|---|
| Starting suspension: | 9.8 × 10$^8$ *Bacillus subtilis*<br>7.6 × 10$^8$ *Staphylococcus aureus*<br>4.9 × 10$^8$ *Pseudomonas fluorescens* |

Example 3

Verification of Applications for the Disinfection of Air Using the Device Represented in FIG. 3

DOA Disinfection of Air

| | |
|---|---|
| Application: | Nebulizing in the ambient air |
| Problem: | Molds and yeasts |
| Dosage: | 0.02 to 0.1 ml of DOA agent per cm$^3$ of air/h (room 32.8 m$^3$ without air conditioning system) |

Performance

| Simulation of the following room climate: | |
|---|---|
| Temperature: | about 25° C. |
| Rel. humidity: | about 55% |

Continuous recirculation of air using the evaporation system shown in FIG. 3; deliberate contamination with *Penicillium commune, Cladosporium suaveolens, Aspergillus niger* and *Saccharomyces cerevisiae* ($5 \times 10^3/m^3$) and continuous nebulizing of the room with DOA disinfection of air using evaporation device. Dosage: 0.02 to 0.1 ml/m³/h of DO agent.

Object/result: Reduction of molds and yeasts (bacteriology: molds and yeasts)

Sampling (RCS and sedimentation plates).

On the day before the application; then daily until a reduction can no longer be established (twice daily in the morning and in the evening sedimentation plates in two places, 1×RCS).

Testing region: Room without air conditioning system, 32.8 m³

Preliminary result:

| RCS device | | Sedimentation plate (30 min) | | | |
|---|---|---|---|---|---|
| yeasts/m³ | molds/m³ | front | | rear | |
| | | yeasts | molds | yeasts | molds |
| 0 | 380 | 0 | 20 | 0 | 14 |

| | |
|---|---|
| Performance: | Artificial loading of the ambient air with *Aspergillus niger, Penicillium commune, Cladosporium suaveolens* and *Saccharomyces cerevisiae* in the morning of day 0. Measurements were performed in the morning and in the afternoon after a fan had been switched on for 5 mm. The DOA nebulization began on day 0 in the afternoon. The result is summarized in Table 3. |
| Comment: | After introduction of the molds and yeasts ($5.2 \times 10^3/m^3$), a reduction to one half of the contaminants ($2 \times 10^3/m^3$) could already be established when DOA nebulization was performed on the same day.<br>On day 2, the molds and yeasts were reduced by about 90% of the starting load, i.e., to $10^2/m^3$.<br>On day 8 (about 1 week), the value was reduced to $10^2$-$10/m^3$, or by 98%.<br>Within the 2nd week, it was found that DOA is capable of maintaining a bioclimate once attained.<br>In practice, this would mean that a long-term application with DOA in the air permanently achieves a low number of molds/yeasts. |

TABLE 3

| | | | Sedimentation plates (exposition time 30 min), YGC agar | | | |
|---|---|---|---|---|---|---|
| | RCS/m³ | | front | | rear | |
| Control day | Molds | Yeasts | Molds | Yeasts | Molds | Yeasts |
| 0 morning | 5270 | — | 356 | — | 360 | — |
| evening | 2273 | — | 41 | 1 | 48 | 1 |
| 1 morning | 655 | 20 | 13 | 32 | 31 | 32 |

TABLE 3-continued

| | | | Sedimentation plates (exposition time 30 min), YGC agar | | | |
|---|---|---|---|---|---|---|
| | RCS/m³ | | front | | rear | |
| Control day | Molds | Yeasts | Molds | Yeasts | Molds | Yeasts |
| evening | 465 | — | 16 | — | 17 | 1 |
| 2 morning | 495 | 25 | 28 | 37 | 22 | 42 |
| evening | 365 | 6 | 13 | — | 12 | — |
| 3 morning | 290 | 25 | 7 | 1 | 12 | — |
| evening | 335 | 10 | 7 | — | 10 | — |
| 4 morning | 420 | — | 18 | — | 22 | — |
| evening | 295 | — | 8 | — | 12 | — |
| 5 morning | 315 | — | 14 | — | 7 | — |
| evening | 345 | 5 | 13 | — | 17 | — |
| 6 morning | 285 | — | 7 | 1 | 1 | — |
| evening | 275 | — | 7 | — | 6 | 1 |
| 7 morning | 185 | 5 | 4 | 5 | 4 | 2 |
| evening | 95 | 30 | 5 | — | 5 | — |
| 8 morning | 105 | — | 1 | — | - | — |
| evening | 85 | — | 4 | — | 3 | — |
| 9 morning | 205 | — | 5 | — | 9 | — |
| evening | 95 | — | 2 | — | 11 | — |
| 10 morning | 85 | — | 4 | 1 | 9 | 1 |
| evening | 90 | — | 6 | — | 7 | — |
| 11 morning | 135 | — | 4 | — | 8 | — |
| evening | 85 | — | 7 | — | 6 | — |
| 12 morning | 70 | — | 4 | 1 | 6 | 2 |
| evening | 90 | — | 11 | — | 8 | — |
| 13 morning | 60 | — | 5 | — | 5 | — |
| evening | 50 | — | 7 | — | 4 | — |

The bubbler DOA system of Example 1 exhibited its highest effectiveness, i.e., a reduction factor $R_f$ of 5 powers of ten (from about 10,000 to 0) already after one day of action. The two-fluid nozzle system of Example 2 shows less effectiveness, but is sufficient. The evaporation system of Example 3 can be employed effectively only for small spaces. The DOA (disinfection of air) agent shows a high efficacy in all systems.

Example 4

Figure 5:
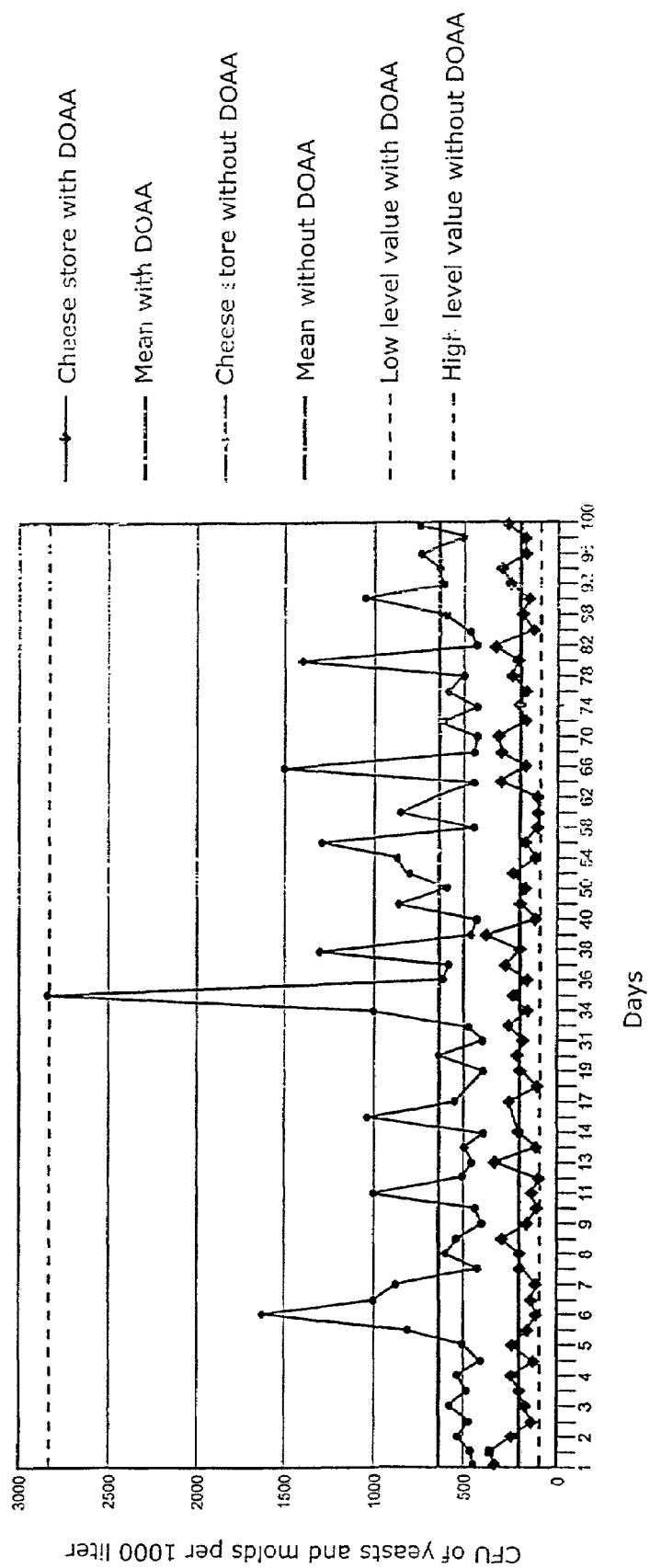

The ambient air of a cheese maturation store was treated with 50 ppt per m³/h of DOA agent according to the method of the invention, and the colony-forming units of molds and yeasts occurring on the maturing cheese were determined over 100 days and compared to those of original cheese store air (without DOA agent). The results are summarized in FIG. 5. The mean value means a germ reduction of about 70%, and the low level value means up to about 99% of germ reduction, which corresponds to clean-room quality for a dosage of 15 ppt of DOA agent.

Example 5

Verification of applications in air for the elimination of pathogens in air using ambient air treatment agents (DOA)

| | |
|---|---|
| Application: | Nebulizing in the ambient air for reducing the number of pathogenic germs |
| Problem: | Generally high number of germs including pathogens in the air, on articles and surfaces, bacteria (Gram-positive and Gram-negative), molds, spore formers and viruses |
| Dosage: | 0.05 ml per m³ of air (1-10 ppb) |

Performance

| Simulation of the following room climate: | |
| --- | --- |
| Temperature: | about 25° C. |
| Rel. humidity: | about 55% |

Continuous recirculation of air using appropriate equipment; deliberate contamination with *Bacillus subtilis, Pseudomonas fluorescens* and *Staphylococcus aureus, Aspergillus niger*, hepatitis B (HBsAg); room continuously treated with fog device using evaporation technique (5 ppb/m$^3$), device contains ambient air treatment agent (Ready for Use/DOA).

Object/result: Reduction of the germ content of the ambient air.

Bacteriology: The tested indicator germs 1-5 are representative of corresponding groups of germs (for example, Bacillaceae group: *Bacillus anthracis*—anthrax/bioweapon; *Bacillus subtilis*—indicator germ). The tests were made with the following indicators:

1. *Staphylococcus aureus*—Gram-positive bacteria
2. *Pseudomonas fluorescens*—Gram-negative bacteria
3. *Aspergillus niger*—molds
4. *Bacillus subtilis*—spore formers
5. Hepatitis B RNA-DNA viruses (HBsAg serum in PBS 1:1)

"In vivo" experimental design and sampling (RCS airborne germ measurements/Biotest Airsamplers).

Germs 1-5 were distributed in the air with starting suspensions ($10^8$/ml as seen from the annex) until $10^4$ germs/m$^3$ were continuosly measured (per germ group 1-5) using a Biotest Airsampler and quantitatively differentiated by microbiological methods in the zero sample (without DOA application/comparative sample). The same experimental design is used with the application of DOA agents in Nos. 1-20 (see Table 4), the DOA agent being continuously spread in the testing zone 2 days before the germs were introduced.

Evaluation

Testing region: Room of 50 m$^3$ without air conditioning system

Continuously treated with 5 ppb/m$^3$ of DOA, depending on the experiment application of DOA 1-20, zero sample without DOA agent.

| | |
| --- | --- |
| Performance: | Artificial loading of the ambient air with $10^4$ germs/m$^3$ each of *Pseudomonas fluorescens, Staphylococcus aureus, Bacillus subtilis, Aspergillus niger*, hepatitis B. Zero sample/Nos. 1-20 DOA applications. After introducing the germs, the air germ content is measured after 24 h using a Biotest Airsampler. |
| Result: | See Table 5 |
| Comment: | In practice, this means that the following results are obtained by application of DOA in the air at 1-10 ppb/m$^3$ (5 ppb): DOA 10-20 is equally effective for all groups of germs, such as: 1. Gram-positive bacteria 2. Gram-negative bacteria 3. Molds 4. Spore formers 5. Viruses |

All formulations contain polyphenol. DOA 1-10 only have partial effects, particular flavoring agents acting at 1-10 ppb/m$^3$ (5 ppb), but becoming altogether synergistically effective.

TABLE 4

Disinfection agents for air (DOA) - composition

| DOA No. | Group of GRAS flavors | % by weight | Components |
| --- | --- | --- | --- |
| 1 | hydrophilic GRAS flavor alcohol | 100 | propylene glycol |
| 2 | aromatic GRAS flavor alcohol | 100 | hydrocinnamic alcohol |
| 3 | hydrophilic GRAS flavor alcohol | 100 | ethanol |
| 4 | aromatic GRAS flavor alcohol | 100 | benzyl alcohol |
| 5 | polyphenols: coffee extract/acid (Coffea SPP), tannin, gallotannic acid | 100 | tannin |
| 6 | essential oil phenolic | 100 | orange oil |
| 7 | essential oil aldehydic | 100 | lemon grass oil |
| 8 | hydrophilic and aromatic GRAS flavor alcohol | 95 / 5 | propylene glycol / benzyl alcohol |
| 9 | hydrophilic and aromatic GRAS flavor alcohol | 95 / 5 | ethanol / hydrocinnamic alcohol |
| 10 | hydrophilic and aromatic GRAS flavor alcohol polyphenol | 92 / 5 / 3 | propylene glycol / benzyl alcohol / tannin |
| 11 | hydrophilic and aromatic GRAS flavor alcohol polyphenol | 92 / 5 / 3 | ethanol / hydrocinnamic alcohol / tannin |
| 12 | hydrophilic and aromatic GRAS flavor alcohol polyphenol essential oil (phenolic) | 91 / 5 / 3 / 1 | propylene glycol / benzyl alcohol / tannin / orange |
| 13 | hydrophilic and aromatic GRAS flavor alcohol polyphenol essential oil (phenolic) | 91 / 5 / 3 / 1 | ethanol / hydrocinnamic alcohol / tannin / orange |
| 14 | hydrophilic and aromatic GRAS flavor alcohol polyphenol essential oil (aldehydic) | 91 / 5 / 3 / 1 | propylene glycol / benzyl alcohol / tannin / lemon grass |

TABLE 4-continued

Disinfection agents for air (DOA) - composition

| DOA No. | Group of GRAS flavors | % by weight | Components |
| --- | --- | --- | --- |
| 15 | hydrophilic and aromatic GRAS flavor | 91 | ethanol |
| | alcohol | 5 | hydrocinnamic alcohol |
| | polyphenol | 3 | tannin |
| | essential oil (aldehydic) | 1 | lemon grass |
| 16 | hydrophilic alcohol | 97 | propylene glycol |
| | polyphenol | 3 | tannin |
| 17 | hydrophilic alcohol | 97 | ethanol |
| | polyphenol | 3 | tannin |
| 18 | aromatic alcohol | 97 | benzyl alcohol |
| | polyphenol | 3 | tannin |
| 19 | aromatic alcohol | 97 | hydrocinnamic alcohol |
| | polyphenol | 2 | tannin |
| 20 | hydrophilic and aromatic alcohol (GRAS flavor) | 90 | propylene glycol |
| | | 5 | benzyl alcohol |
| | polyphenol | 3 | tannin |
| | flavor acids | 1 | lactic acid |

TABLE 5

Air-borne germ measurement
Examination results: disinfectant for air (DOA)

RCS/Biotest air-borne germ measurement/$m^3$

| DOA No. | Gram-positive bacteria | Gram-negative bacteria | molds | spore formers | RNA/DNA viruses |
| --- | --- | --- | --- | --- | --- |
| 1 | +++ | +++ | ++ | ++++ | ++++ |
| 2 | +++ | ++++ | +++ | ++++ | ++++ |
| 3 | ++++ | ++++ | ++++ | ++++ | ++++ |
| 4 | +++ | ++++ | +++ | ++++ | ++++ |
| 5 | ++++ | ++++ | +++ | ++++ | ++++ |
| 6 | ++++ | ++++ | ++++ | ++++ | ++++ |
| 7 | ++++ | ++++ | ++++ | ++++ | ++++ |
| 8 | ++ | +++ | +++ | ++++ | ++++ |
| 9 | +++ | ++++ | ++++ | ++++ | ++++ |
| 10 | + | + | + | + | + |
| 11 | + | + | + | + | + |
| 12 | + | + | + | + | + |
| 13 | + | + | + | + | + |
| 14 | + | + | + | + | + |
| 15 | + | + | + | + | + |
| 16 | + | + | + | + | + |
| 17 | + | + | + | + | + |
| 18 | + | + | + | + | + |
| 19 | + | + | + | + | + |
| 20 | + | + | + | + | + |

Starting suspension:
$8.7 \times 10^8$ *Bacillus subtilis* (ATCC)
$5.1 \times 10^8$ *Staphylococcus aureus* (ATCC)
$4.4 \times 10^8$ *Pseudomonas fluorescens* (ATCC)
$3.8 \times 10^8$ *Aspergillus niger* (ATCC)
$2.0 \times 10^6$ hepatitis B (HBsAg)
Legend:
++++ germ reduction 0/$m^3$
+++ germ reduction from $10^4$ to $10^3/m^3$
++ germ reduction from $10^4$ to $10^2/m^3$
+ germ reduction from $10^4$ to $10^1/m^3$ From the results obtained for indicator germs 1 to 5, it is documented that the antimicrobial compositions are suitable for the removal of the following germs/groups of germs from air:

Bacteria and spore formers: Pseudomonaceae, Spirillaceae, Achromobacteriaceae, Brucellaceae, Bacteriodaceae, Micrococcaceae, Neisseriaceae, Lactobacillaceae, Corynebacteriaceae, Bacillaceae, Mucobacteriaceae, Actinomycetaceae, Terponemataceae, Mycoplasmataceae, Rikettsiaceae, Bartonellaceae.

RNA viruses: picorna viruses, reoviruses, arboviruses, myxoviruses, paramyxoviruses, rhabdoviruses, leukoviruses, rubella virus, corona viruses.

Molds and fungi: dermatophytes, skin fungi, yeasts, molds.

DNA viruses: picorna viruses, papova viruses, adenoviruses, herpes viruses, smallpox viruses, non-classified PLT, mycoplasmas.

The invention claimed is:

1. A method for the disinfection of air, comprising the distributing or atomizing of an antimicrobial composition, wherein a concentration of the antimicrobial composition of from 0.001 to 1 ml per $m^3$ of air is adjusted by said distributing or atomizing of said antimicrobial composition, and/or exchanging air systems are adjusted to achieve a dosage of from 0.001 to 1 ml per $m^3$ of air per hour, and/or a permanent concentration of from 5 to 10 ppb of the antimicrobial composition is achieved, wherein said antimicrobial composition is free from ethanol and isopropanol and comprises
    (a) at least 75% by weight of propylene glycol; and
    (b) 0.01 to 25% by weight of tannic acid.

2. The method according to claim 1, wherein said antimicrobial composition further comprises benzyl alcohol.

3. The method according to claim 2, wherein said antimicrobial composition comprises from 0.1 to 10% by weight benzyl alcohol.

4. The method according to claim 1, wherein the antimicrobial composition further comprises lactic acid.

5. The method according to claim 2, wherein said antimicrobial composition comprises form 0.1 to 10% by weight of benzyl alcohol and from 90 to 99.9% by weight of propylene glycol.

6. The method according to claim 1, wherein said antimicrobial composition further comprises GRAS flavoring agents selected from (c) phenols, (d) esters, (e) terpenes, (f) acetals, (g) aldehydes, and (h) essential oils.

7. The method according to claim 6, wherein said antimicrobial composition contains from 0.001 to 25% by weight of said additional GRAS flavoring agents (c) to (h).

8. The method according to claim 6, wherein said additional GRAS flavoring agents are phenols (c) and/or essential oils (h).

9. The method according to claim 1, wherein said antimicrobial composition does not contain any derivatives of said GRAS flavoring agents.

10. The method according to claim 2, wherein said antimicrobial composition comprises from 0.1 to 20% by weight of benzyl alcohol and from 0.01 to 10% by weight of tannic acid.

11. The method according to claim 5, wherein the antimicrobial composition further comprises water and water content of said antimicrobial composition is less than 35% by weight.

12. The method according to claim 1, wherein said composition further comprises emulsifiers, stabilizers, antioxidants, preservatives, solvents, and/or carrier materials.

13. The method according to claim 1, wherein said atomizing of said antimicrobial composition effected by a two-fluid nozzle system, evaporation system or a bubbler installation for the air, or in a special design for packaging.

14. The method according to claim 1, wherein the concentration of said antimicrobial composition from 0.01 to 0.1 ml per $m^3$ of air is adjusted by said distributing or atomizing of said antimicrobial composition, and/or exchanging air systems are adjusted to achieve a dosage of from 0.01 to 0.1 ml per $m^3$ of air per hour.

15. A method for the disinfection of air to reduce the concentration of germs selected from the group consisting of at least one of gram-positive bacteria, gram-negative bacteria, molds, spore-formers and viruses, said method comprising the distributing or atomizing of an antimicrobial composition, wherein a concentration of the antimicrobial composition of from 0.001 to 1 ml per $m^3$ of air is adjusted by said distributing or atomizing of said antimicrobial composition, and/or exchanging air systems are adjusted to achieve a dosage of from 0.001 to 1 ml per $m^3$ of air per hour, and/or a permanent concentration of from 5 to 10 ppb of the antimicrobial composition is achieved, wherein said antimicrobial composition is free from ethanol and isopropanol and comprises (a) at least 75% by weight of propylene glycol; and
(b) 0.01 to 25% by weight of tannic acid.

16. A method for the disinfection of air to reduce the concentration of germs selected from the group consisting of at least one of *bacillus subtilis, pseudomona fluorescens, staphylococcus aureus, aspergillus niger* and hepatitis B, said method comprising the distributing or atomizing of an antimicrobial composition, wherein a concentration of the antimicrobial composition of from 0.001 to 1 ml per $m^3$ of air is adjusted by said distributing or atomizing of said antimicrobial composition, and/or exchanging air systems are adjusted to achieve a dosage of from 0.001 to 1 ml per $m^3$ of air per hour, and/or a permanent concentration of from 5 to 10 ppb of the antimicrobial composition is achieved, wherein said antimicrobial composition is free from ethanol and isopropanol and comprises (a) at least 75% by weight of propylene glycol; and
(b) 0.01 to 25% by weight of tannic acid.

17. A method for the disinfection of air to reduce the concentration of *bacillus anthracis*, said method comprising the distributing or atomizing of an antimicrobial composition, wherein a concentration of the antimicrobial composition of from 0.001 to 1 ml per $m^3$ of air is adjusted by said distributing or atomizing of said antimicrobial composition, and/or exchanging air systems are adjusted to achieve a dosage of from 0.001 to 1 ml per $m^3$ of air per hour, and/or a permanent concentration of from 5 to 10 ppb of the antimicrobial composition is achieved, wherein said antimicrobial composition is free from ethanol and isopropanol and comprises (a) at least 75% by weight of propylene glycol; and
(b) 0.01 to 25% by weight of tannic acid.

18. The method according to claim 16, wherein said antimicrobial composition further comprises benzyl alcohol.

19. The method according to claim 18, wherein the alcohol constituent of said antimicrobial composition comprises from 1% to 10% by weight of benzyl alcohol.

20. The method according to claim 16, wherein said antimicrobial composition further comprises lactic acid.

21. The method according to claim 15, wherein said antimicrobial composition further comprises lactic acid.

\* \* \* \* \*